(12) United States Patent
Ainsworth et al.

(10) Patent No.: US 7,532,920 B1
(45) Date of Patent: May 12, 2009

(54) GUIDEWIRE WITH OPTICAL FIBER

(75) Inventors: Robert D. Ainsworth, Scotts Valley, CA (US); Deborah Kilpatrick, Mountain View, CA (US); Jeong S. Lee, Diamond Bar, CA (US); Bridget A. Hurley, Mountain View, CA (US); Jeffrey T. Ellis, Mountain View, CA (US); Marc Jalisi, Temecula, CA (US); Florencia Lim, Union City, CA (US); Chi Long, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 677 days.

(21) Appl. No.: 09/872,216

(22) Filed: May 31, 2001

(51) Int. Cl.
*A61B 5/00* (2006.01)
*A61B 6/00* (2006.01)
*A61B 5/02* (2006.01)

(52) U.S. Cl. ............... 600/342; 600/341; 600/478; 600/505

(58) Field of Classification Search ........... 600/101, 600/104, 114, 117, 121, 125, 178, 182, 300, 600/342, 373, 424, 425, 470, 476, 547, 549, 600/461, 407, 310, 322, 339, 340, 341, 473, 600/485, 486, 504, 505, 585; 604/264, 272
See application file for complete search history.

(56) References Cited

U.S. PATENT DOCUMENTS

| 4,587,972 | A |   | 5/1986  | Morantte, Jr.          |
|-----------|---|---|---------|------------------------|
| 4,619,274 | A | * | 10/1986 | Morrison ........ 600/585 |
| 4,671,288 | A |   | 6/1987  | Gough                  |
| 4,794,931 | A |   | 1/1989  | Yock                   |
| 4,830,460 | A | * | 5/1989  | Goldenberg ..... 385/118 |
| 4,841,977 | A |   | 6/1989  | Griffith et al.        |
| 4,887,605 | A |   | 12/1989 | Angelsen et al.        |
| 4,920,967 | A |   | 5/1990  | Cottonaro et al.       |
| 4,926,875 | A |   | 5/1990  | Rabinovitz et al.      |
| 4,941,473 | A | * | 7/1990  | Tenerz et al. ..... 600/486 |
| 5,022,399 | A |   | 6/1991  | Biegeleisen            |
| 5,047,213 | A |   | 9/1991  | Finlan et al.          |
| 5,167,233 | A |   | 12/1992 | Eberle et al.          |
| 5,178,153 | A | * | 1/1993  | Einzig ............ 600/505 |
| 5,284,146 | A |   | 2/1994  | Czar et al.            |

(Continued)

OTHER PUBLICATIONS

Beekhuizen H, van Furth R. "Monocyte Adherence to Human Vascular Endothelium." *Journal of Leukocyte Biology* 1993, vol. 54, 363-378.

(Continued)

*Primary Examiner*—Eric F Winakur
*Assistant Examiner*—Michael T Rozanski
(74) *Attorney, Agent, or Firm*—Fulwider Patton LLP (57) ABSTRACT

Apparatus and method to perform therapeutic treatment and diagnosis of a patient's vasculature through the use of an intravascular device having an optical fiber disposed therein. In an embodiment of this invention, the apparatus includes a therapeutic guidewire and at least one optical fiber disposed through the therapeutic guidewire, the optical fiber capable of providing diagnostic information before, during, and after the therapeutic treatment. In an embodiment, diagnostic information includes vessel and blood characteristics such as hemodynamic characteristics, hematological parameters related to blood and blood components, and thermal parameters of the vasculature.

24 Claims, 5 Drawing Sheets

U.S. PATENT DOCUMENTS

| | | | |
|---|---|---|---|
| 5,325,860 | A | 7/1994 | Seward et al. |
| RE34,695 | E | 8/1994 | Mar et al. |
| 5,345,940 | A | 9/1994 | Seward et al. |
| 5,372,138 | A | 12/1994 | Crowley et al. |
| 5,487,972 | A | 1/1996 | Gelfand et al. |
| 5,571,086 | A | 11/1996 | Kaplan et al. |
| 5,582,171 | A | 12/1996 | Chornenky et al. |
| 5,599,492 | A * | 2/1997 | Engelson ............ 264/167 |
| 5,601,087 | A | 2/1997 | Gunderson et al. |
| 5,603,820 | A | 2/1997 | Malinski et al. |
| 5,693,043 | A | 12/1997 | Kittrell et al. |
| 5,744,902 | A | 4/1998 | Vig |
| 5,752,518 | A | 5/1998 | McGee et al. |
| 5,756,351 | A | 5/1998 | Isacoff et al. |
| 5,782,760 | A | 7/1998 | Schaer |
| 5,848,969 | A | 12/1998 | Panescu et al. |
| 5,855,563 | A | 1/1999 | Kaplan et al. |
| 5,873,835 | A | 2/1999 | Hastings et al. |
| 5,876,345 | A | 3/1999 | Eaton et al. |
| 5,902,308 | A | 5/1999 | Murphy |
| 5,908,445 | A | 6/1999 | Whayne et al. |
| 5,919,129 | A | 7/1999 | Vandre |
| 5,935,075 | A | 8/1999 | Casscells et al. |
| 5,938,595 | A | 8/1999 | Glass et al. |
| 5,951,471 | A | 9/1999 | de la Rama et al. |
| 5,951,482 | A | 9/1999 | Winston et al. |
| 5,957,903 | A | 9/1999 | Mirzaee et al. |
| 5,980,471 | A | 11/1999 | Jafari |
| 5,984,909 | A | 11/1999 | Lurie et al. |
| 6,001,085 | A | 12/1999 | Lurie et al. |
| 6,023,638 | A | 2/2000 | Swanson |
| 6,134,003 | A | 10/2000 | Terney et al. |
| 6,141,576 | A | 10/2000 | Littmann et al. |
| 6,178,346 | B1 * | 1/2001 | Amundson et al. .......... 600/473 |
| 6,445,939 | B1 | 9/2002 | Swanson et al. |
| 6,458,088 | B1 * | 10/2002 | Hurtak et al. ............... 600/585 |
| 6,463,317 | B1 | 10/2002 | Kucharczyk et al. |
| 6,498,941 | B1 | 12/2002 | Jackson |
| 6,605,111 | B2 | 8/2003 | Bose et al. |
| 6,697,667 | B1 | 2/2004 | Lee et al. |
| 6,716,178 | B1 | 4/2004 | Kilpatrick et al. |
| 6,947,787 | B2 | 9/2005 | Webler |
| 7,025,734 | B1 | 4/2006 | Ellis et al. |
| 2006/0129041 | A1 | 6/2006 | Ellis et al. |

OTHER PUBLICATIONS

Casscells W, Hathorn B, David M, Krabach T, Vaugh W, Mcallister H, et al., "Thermal detection of Cellular Infiltrates in Living Atherosclerotic Plaques: Possible Implications for Plaque Rupture and Thrombosis," *Lancet* 1996. vol. 347, 1447-1451.

Einav S. "Laser Doppler Fiberscope Anemometer for In Vivo Blood Flow Measurements." *Optical Fibers in Medicine VIII* 1993, 62-73.

Hangiandreou N, Toggart E, Mistretta C. "Investigation of the Performance of Two Types of the Doppler Catheter in Vitro." *Catherization and Cardiovascular Diagnosis* 1989, vol. 18, 108-117.

Ikeda U, Takahashi M, Shimada K. "Monocyte-Endothelial Cell Interaction in Atherogenesis and Thrombosis." *Clinical Cardiology* 1997, vol. 21, 11-14.

Kern M, de Bruyne B, Pijls N. "From Research to Clinical Practice: Current Role of Intracoronary Physiologically Based Decision making in the Cardiac Catherterization Laboratory." *Journal of the American College of Cardiology* 1997, vol. 30 613-620.

Kilpatrick D, Kajiya F, Ogasawara Y. "Fiber Optic Laser Doppler Measurement of Intravascular Velocity." *Australasian Physical and Engineering Sciences in Medicine* 1998, vol. 11, 5-14.

Nishhara H, Koyama J, Hoki N, Kajiya F, Hironaga M, Kano M. "optical-Fiber Laser Doppler Velocimeter for High-Resolution Measurement of Pulsatile Blood Flows." *Applied Optics* 1982, vol. 21, 1785-1790.

Serruys P, di Mario C, Piek J, Shcroeder E, Vrints C, Probst P, de Bruyne B, et al., "Prognostic Value of Intracoronary Flow Velocity and Diameter Stenosis in Assessing the Short—and Long-Term Outcomes of Coronary Balloon Angioplasty: *The Debate Study*." *Circulation* 1997, vol. 96, 3369-3377.

Stefandadis C, Diamantopoulos L, Vlachopoulos C, Tsiamis E, Dernellis J, Toutouzas K, et al. "Thermal Heterogeneity Within Human Atherosclerotic Coronary Arteries Detected In Vive: A New Method of Detection by Application of a Special Thermography Catheter." *Circulation* 1999, vol. 99, 1965-71.

Doucette J., Corl D., Payne H., Flynn A., Goto M., Nassi M., Segal J. "Validation of a Doppler Guidewire for Intravascular Measurement of Coronary Artery Flow Velocity", Circulation 1992, vol. 85, 382-385.

Dib N., Bajwa T., Shalev Y., Nesto R. Schmidt D., "Validation of Doppler Flo Wire for Measurement of Coronary Flow Reserve in Humans". *Catheterization and Cardiovascular Diagnosis* 1998, vol. 45, 382-385.

Pijls N., Van Gelder., Van der Voort P., Peels K., Bracke F., Bonnier H., El Gamal M., "Fractional Flow Reserve: A Useful Index to Evaluate the Influence of an Epicardial Coronary Stenosis on Myocardial Blood Flow." *Circulation* 1995, vol. 92, 3183-3193.

Bridget Hurley's Lab Book 5449, pp. 28-29.

Jeff Ellis Lab Book 5528, pp. 103-107.

Davis R., "Bursting the Deadly Danger Of Aortic Aneurysms", *USA Today*, Mar. 16, 2000, Section 10D.

Krohn D., "Two Ways of Sensing with Fibers for Two Kinds of Applications", 1998 *The Photonics Design and Applications Handbook*, Sensors, H-203.

Engineering & Marketing Staff, "An Introduction to Fiber Optics", 1998 *The Photonics Design and Applications Handbook*, Fiber Optics. H-176.

Bhatia V., Murphy K., de Vires M., Sen M., D'Alberto T., "A Comparative Evaluation of the Types and Applications of Various Sensors" 1998, *The Photonics Design and Applications Handbook*, Sensors, H-199.

McCann B., "Three Silica-Core Fibers Rise to Top in Medical Laser Uses", 1998, *The Photonics Design and Applications Handbook*, Fibers/Medical Lasers, H-209.

McCann B., "Fiber Holds the Key to Medical Lasers' Success", May 1990, *Photonics Spectra*, p. 127.

Moslem A., "Transmission properties of optical fibers at two laser wavelengths: 660 nm & 2100 nm", PTICAL Materials, Aug. 19, 1991, Center for Laser Research, Oklahoma State University, p. 27-41.

* cited by examiner

GUIDEWIRE WITH OPTICAL FIBER

FIELD OF THE INVENTION

This invention relates to the field of medical diagnosis and treatment by means of an intravascular device incorporating a sensor. More specifically, the present invention relates to a treatment guidewire incorporating an optical fiber capable of providing diagnostic information before, during, and after the procedure.

DESCRIPTION OF RELATED ART

Arteriosclerosis, or more specifically atherosclerosis, is a common human ailment arising from the deposition of fatty-like substances, referred to as atheroma or plaque, on the walls of systemic, peripheral, and coronary blood vessels. When deposits accumulate in localized regions of a vessel, blood flow can be occluded or restricted, increasing the risk of heart attack or stroke.

Numerous approaches for reducing and removing such vascular deposits have been proposed, including balloon angioplasty, where a balloon-tipped catheter is used to dilate a region of atheroma; atherectomy, where a blade or other cutting element is used to sever and remove the atheroma; and laser angioplasty, where laser energy is used to ablate (i.e., remove) at least a portion of the atheroma. The vast majority of these therapeutic devices, however, are being used with very little information about the in vivo biological environment, including for example, the hemorheology, vascular biology or histology and histochemistry of the vasculature being treated. Without such information available to the cardiologist, "lesion specific" treatment, as well as preventive measures, cannot be adequately envisioned or planned.

To aid the vascular therapeutic approaches above, a number of techniques for transluminal imaging of the atheroma (and other diseased regions) or for pressure and/or flow measurements of a blood vessel have been proposed. Some of the imaging techniques include endoscopic and ultrasonic imaging techniques involving the use of an intravascular device, such as a catheter, positioned at a desired location within the blood vessel to be treated or imaged. Techniques developed for measuring blood pressure and flow involve the use of intravascular devices, such as catheters and/or guidewires, having a ferrofluid-type pressure transducer and an anemometer-type flow transducer or intravascular devices incorporating an ultrasound Doppler-type design.

Many of these diagnostic devices have limitations that require measurement of properties such as pressure or flow rate at locations far removed from the specific site of disease. Therefore, merely using the device already compromises accurate diagnosis. Furthermore, because most of the diagnostics are not part of the therapeutic phase, the diagnostic device must be removed in order to treat the patient with, for example, a balloon catheter or stent. Previous attempts to design a combined diagnostic-therapeutic device have yielded devices either too bulky or too cumbersome to use during procedures, while in other cases, the cost of devices and auxiliary systems has prevented widespread use by the cardiology community. The result is that therapeutic strategies are often unilaterally rendered without relevant information concerning the lesion, surrounding vasculature, or the biomechanical environment—information which, if available, could be appropriately used to improve both acute and chronic outcomes for the patient.

In the medical field, both optical and non-optical fibers have been used on device platforms. Optical fibers have generally been used to illuminate and view various interior parts of the human body. Example devices include fiber optic scopes. In some medical applications, non-optic fiber-based devices have been combined with guidewire devices and then used to diagnose or treat conditions within patients. One such example is a guidewire that measures blood flow velocity in coronary arteries using an ultrasound Doppler mechanism. Another example is a Doppler interferometric imaging apparatus containing a fiber optic interferometer and an imaging guidewire. One more example is a guidewire system that includes an interferometric fiber optic guidance system (for the guidewire) and a tissue removal member. In each of the above-described systems, however, the device either utilizes a non-optical fiber or the device utilizing optical fibers is specific to either diagnosis or treatment of a previously diagnosed condition, not for performing combined diagnosis/treatment applications.

SUMMARY OF THE INVENTION

The present invention directs to an apparatus that performs therapeutic treatment and diagnosis of a patient's vasculature through the use of an intravascular device having an optical fiber disposed therein. In an embodiment of this invention, the apparatus includes a therapeutic guidewire and at least one optical fiber disposed through the therapeutic guidewire, the optical fiber configured to provide diagnostic information before, during, and after a therapeutic treatment. In an embodiment, diagnostic information includes vessel and blood characteristics such as hemodynamic characteristics, hematological parameters related to blood and blood components, and thermal parameters of the vasculature.

BRIEF DESCRIPTION OF THE DRAWINGS

The present invention is illustrated by way of example and not limitation in the accompanying figures.

DETAILED DESCRIPTION OF THE INVENTION

An apparatus and method to perform therapeutic treatment and diagnosis of a patient's vasculature through the use of a therapeutic guidewire having at least one optical fiber disposed therethrough are described.

In the following detailed description, numerous specific details are set forth in order to provide a more thorough understanding of the present invention. However, it will be apparent to those skilled in the art to which this invention pertains that the present invention may be practiced without these specific details. In other instances, well-known devices, methods, procedures, and individual components have not been described in detail so as not to obscure aspects of the present invention.

FIGS. 1-4 illustrate generally an apparatus 1 embodying features of the present invention. In an embodiment of this invention, apparatus 1 includes a therapeutic guidewire 10 to perform a therapeutic treatment and at least one optical fiber 30 longitudinally disposed within a lumen (or channel) 23 of therapeutic guidewire 10 configured to provide diagnostic information before, during, and after the therapeutic treatment. Guidewire 10 may be used for treatment and diagnosis of a patient's vascular system, as well as of body organs and structures such as the esophagus, the stomach, the colon, the uterus, saphenous vein grafts, heart valves. Any type and/or shape therapeutic guidewire 10 known in the art may be used within the scope of this invention.

Figure 1:
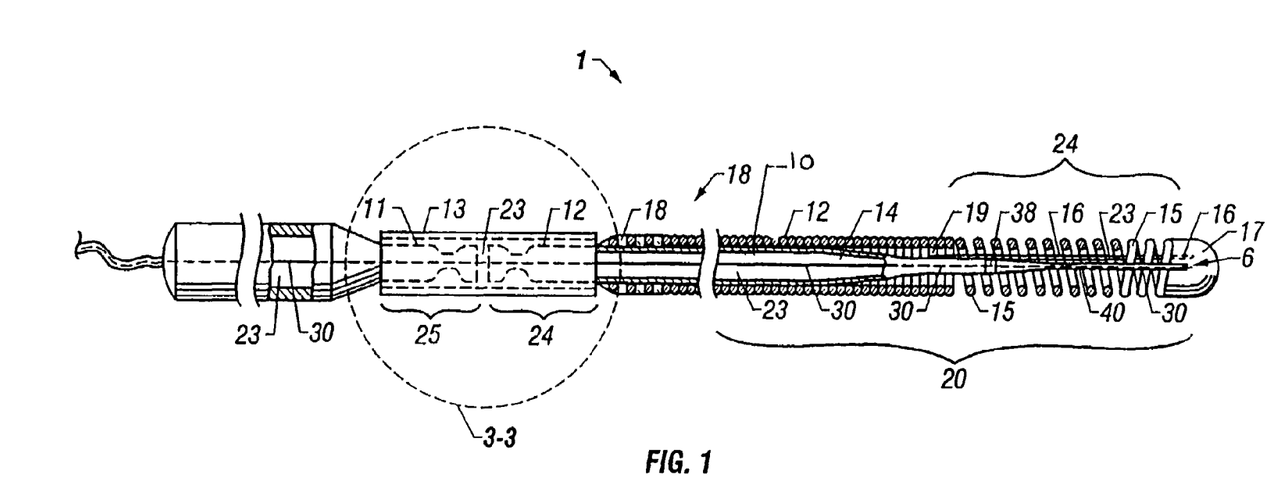
FIG. 1 is a schematic side view showing a partial cross section of an embodiment of a therapeutic guidewire with optical fiber of the present invention.

The optical fiber 30 may be fixedly coupled to the therapeutic guidewire 10 at least at one coupling location 40 on the therapeutic guidewire 10. Alternatively, the optical fiber 30 may be operatively coupled to the therapeutic guidewire 10. In this configuration, the optical fiber 30 is generally movable, e.g. slideable, within the therapeutic guidewire 10.

Typically, the optical fiber 30 filament is made of at least two concentrically arranged elements: a central core and a cladding surrounding the core. The "functional" part of the optical fiber is the core—the part that actually transmits the light. The core is made of drawn or extruded silica (glass) or plastic, although other materials may be used. The cladding is usually made of the same material as the core, but with slightly lower index of refraction. This index difference causes total internal reflection to occur within the optical fiber so that the light is transmitted down the fiber and does not escape through the side walls of the optical fiber. During use, the core of the optical fiber 30 transmits light radiation signals from a light source, for example a laser, to the distal tip of the optical fiber and then into the vasculature of a patient. The distal tip of the optical fiber core is generally exposed to, or in optical contact with the vasculature of a patient. Light radiation signals reflected back by various structures or elements, e.g. blood particles, present in the vasculature are then transmitted via the optical fiber back to a detector in a laser/data processing system.

In one embodiment, the optical fiber(s) 30 described above has an outer diameter in the range of approximately 30 to 250 microns; however, other optical fiber diameters are within the scope of this invention. It should be noted that the diameter of the optical fiber core generally has a much lower diameter, for example in the range of about 5-25 microns.

During a medical procedure, a portion of the optical fiber(s) 30 may be exposed within a body lumen of a patient, such as blood vessel, at least at one location of the therapeutic guidewire 10. The optical fiber(s) 30 is configured to provide the therapeutic guidewire 10 with the ability to sense vessel and blood characteristics, including but not limited to hemodynamic characteristics, hematological parameters related to blood and blood components, and thermal parameters of the vasculature, lesion, or body site being treated.

Possible target hemodynamic characteristics or variables include blood flow velocity and velocity profile characteristics. The detection of stagnant or recirculating flow regions may relate to propensity of cell adhesion to the endothelium, whereas the detection of slightly turbulent flow may indicate a stenosis that could be angiographically silent. In addition, the levels of shear force may be important for detecting disease-prone regions or shear-induced platelet activation. There are other hemodynamic variables, such as local pressure gradient, that could also be measured or derived from measurements by the optical fiber of the present invention with the intent of identifying regions at high risk for clinical complication.

As stated above, optical fiber 30 disposed within the therapeutic guidewire 10 is configured to sense and thus may be used to measure or allow measurement of temperature, pressure, flow, velocity, turbulence, shear stress, etc., of a treatment site. A physician may then use this information in making treatment decisions. For example, if the optical fiber 30 identifies flow discontinuities or abnormal flow rates and the therapeutic guidewire 10 is operatively coupled to a balloon catheter, the physician could use this information to optimize an angioplasty. Or, if the optical fiber 30 is disposed within a therapeutic guidewire 10 that is used as a stent delivery system, the physician can use the information to optimize the dilatation of the stent.

Furthermore, the optical fiber described above may be incorporated in intravascular devices to address numerous clinical challenges. Such clinical challenges may include, but are not limited to, the prevention and/or treatment of restenosis, chronic total occlusion, saphenous vein graft (SVG) disease, acute myocardial infarction, restenotic lesions, small vessels, dissections, long lesions and diffuse disease, acute or threatened closure, bifurcation lesions, ostial lesions, left main coronary artery (LMCA) disease, aneurysms, vulnerable plaques, etc.

In one embodiment, the optical fiber(s) 30 is exposed to a blood vessel of a patient at the distal tip 6 of the therapeutic guidewire 10. Alternatively, the therapeutic guidewire 10 may have at least one opening 38, such as a window or a cutaway in its wall that allows the optical fiber 30 to be exposed to a patient's vasculature and perform its intended sensing function, i.e., investigating, detecting, and/or measuring the particular physical characteristics or variables within a patient's vasculature.

Depending on the type of application in which is to be used, the therapeutic guidewire 10 is operatively coupled to a variety of intravascular/intraluminal treatment devices, including for example a balloon dilatation catheter for percutaneous transluminal coronary angioplasty (PTCA) and percutaneous transluminal angioplasty (PTA) procedures, an intravascular/intraluminal stent, a directional atherectomy device, a drug delivery device, a radiation treatment device, or any other intravascular/intraluminal treatment device used in the art.

Continuing with reference to FIG. 1, in one embodiment, the therapeutic guidewire 10 includes an elongated core member that has a relatively high strength proximal core section 11 and a relatively short flexible distal core section 12.

Depending on manufacturing preferences, type of application used, etc., therapeutic guidewire 10 may include a connecting element 13 that joins a distal end 25 of the proximal core section 11 and a proximal end 24 of the distal core section 12 of therapeutic guidewire 10. At least one optical fiber 30 extends longitudinally through a lumen 23 present in and common to the proximal core section 11, the connecting element 13 and the distal core section 12. Alternatively, the optical fiber 30 may extend longitudinally along the outside of the proximal core section 11, the connecting element 13 and the distal core section 12.

Figure 12:
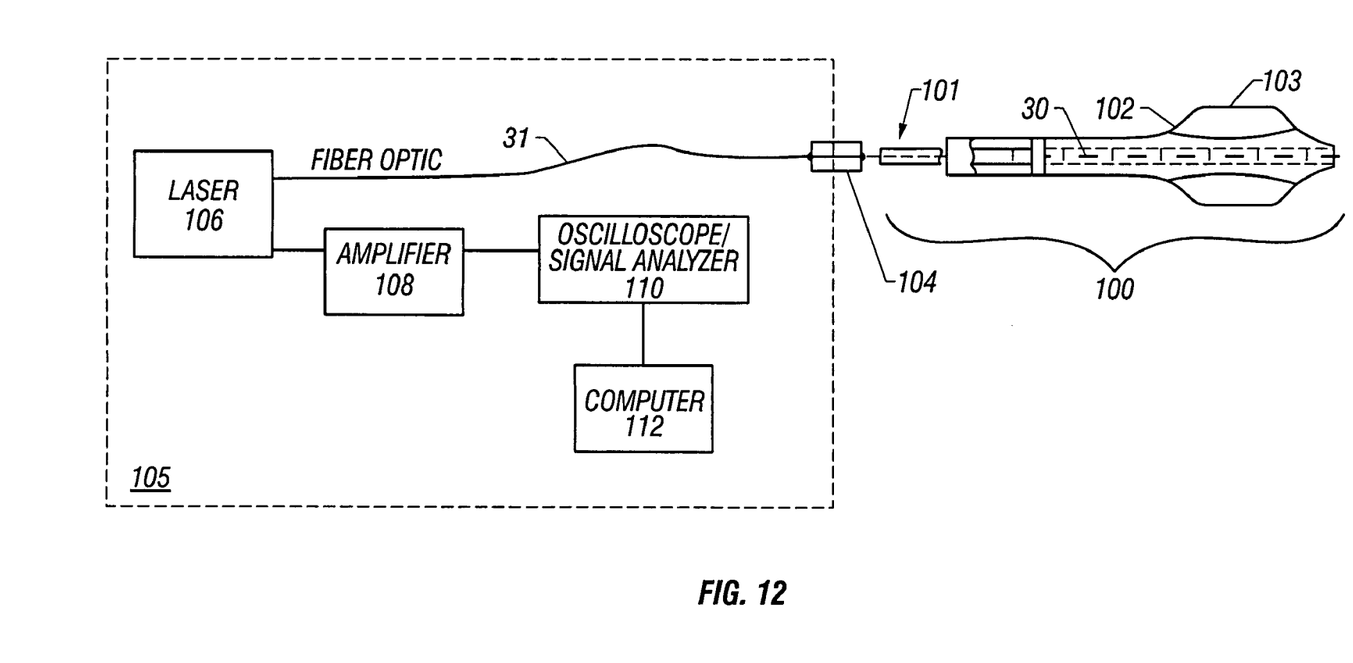
FIG. 12 is a block schematic diagram of an embodiment of a therapeutic guidewire-based therapeutic treatment system of the present invention coupled to a data processing system.

Optical fiber 30 may generally extend slightly beyond both the proximal and distal ends of therapeutic guidewire 10. The proximal extension of the optical fiber 30 would allow for connection of the optical fiber 30 to a data processing system (shown in FIG. 12) through a mechanical coupler (as shown in FIG. 12). The distal extension of the optical fiber 30 would allow for necessary steps required to make the optical fiber 30 tip flush with, or extend slightly beyond the distal end portion 20 of the therapeutic guidewire 10.

In one embodiment, proximal core section 11 and distal core section 12 are each formed from a hypotube made of stainless steel (SS) or of a pseudoelastic alloy material, such as Nickel-Titanium (Ni—Ti) alloy (e.g., Nitinol). The connecting element 13 is configured as a sleeve or hollow member that slightly overlaps the distal end 25 of proximal core section 11 and the proximal end 24 of distal core section 12. It should be noted that various configurations and/or shapes may be practiced within the scope of this invention (as shown in detail in FIGS. 3, 6 and 7).

Continuing with reference to FIG. 1, in the embodiment shown, the distal core section 12 has at least one tapered section 14 that becomes smaller in the distal direction. The tapered shape of distal core section 12 enhances the mechanical performance of the therapeutic guidewire 10. Alternatively, the distal core section 12 may have a non-tapered shape, which generally simplifies the therapeutic guidewire manufacturing process.

A flexible coil 15, generally having a helical configuration, is disposed about the distal core section 12. Flexible coil 15 may be secured at its distal end to the distal end of a shaping ribbon 16 by a mass of bonding material, such as solder, which forms rounded tip 17 when it solidifies. The proximal end of the flexible coil 15 is secured to the distal core section 12 at a proximal location 18 and at intermediate location 19 by a suitable bonding material, e.g. solder. The proximal end of the shaping ribbon 16 is secured to the distal core section 12 at the same intermediate location 19 by the bonding material, e.g. solder. The most distal section 21 of the flexible coil 15 may be made of radiopaque metal, such as platinum or platinum-nickel alloys, to facilitate the fluoroscopic observation thereof while it is disposed within a patient's body.

As stated above, in one embodiment, the optical fiber(s) 30 is exposed to a blood vessel of a patient at the distal tip 6 of the therapeutic guidewire 10. Alternatively, the therapeutic guidewire 10 may have at least one opening 38, such as a window or a cutaway in its wall that allows the optical fiber 30 to be exposed to a patient's vasculature and perform its intended sensing function, i.e., investigating, detecting, and/ or measuring the particular physical characteristics or variables within a patient's vasculature. Opening/window 38 may have any size and/or shape that is advantageous to optical fiber 30, therapeutic guidewire 10 and/or guidewire manufacturing preferences. Alternatively, the optical fiber 30 may be exposed to a patient's vasculature through therapeutic guidewire coil 15.

Figure 2:
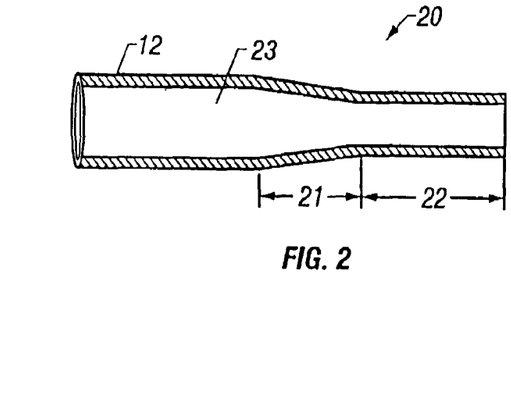
FIG. 2 is a schematic side view cross section of an embodiment of the distal end core section of therapeutic guidewire of FIG. 1.
Figure 5:
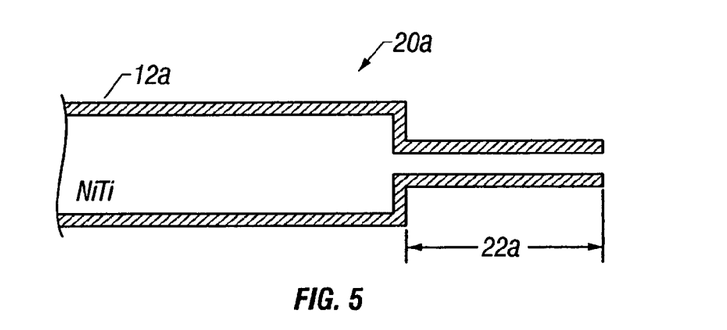
FIG. 5 is a schematic side view cross section of an alternate embodiment of the distal core section of a therapeutic guidewire practicing this invention.

With reference to FIGS. 1 and 2, the most distal part 20 of the distal core section 12 may be tapered and plunge-ground to a specific length, plunge-ground to a specific length only (as shown in FIG. 5), or flattened into a rectangular cross-section (not shown). In the embodiment shown in FIG. 2, the most distal part 20 of the distal core section 12 has a taper length 21 and a distal plunge-ground length 22. Taper length 21 is typically in the range of approximately 4 to 7 cm, while distal plunge-ground length 22 is typically in the range of approximately 6 to 10 cm. In one configuration, taper length 21 is approximately 5 cm and distal plunge-ground length 22 is approximately 5 cm. The outer diameter of the plunge-ground portion of the most distal part 20 is in the range of approximately 0.006 to 0.018 in., with one embodiment having an outer diameter of approximately 0.0105 in. For the alternative embodiment having the most distal part 20a of the distal core section 12a just plunge-ground to a specific length (as shown in FIG. 5), distal plunge-ground length 22a is the range of approximately 1.7 to 2.2 cm, and preferably about 2 cm.

If desired, the most distal part 20 of the distal core section 12 may also be provided with a rounded tip made out of solder or other suitable material to prevent its passage through the spacing between the stretched distal section 21 of the flexible coil 15 (shown in FIG. 1).

Continuing with reference to FIG. 1, the distal core section 12 is preferably made of a pseudoelastic alloy material, such as Nickel-Titanium (Ni—Ti) alloy (e.g., Nitinol). In one embodiment, the Ni—Ti alloy material consisting essentially of about 30 to about 52% titanium and the balance nickel and up to 10% of one or more other alloying elements. The other alloying elements may be selected from the group consisting of iron, cobalt, vanadium, platinum, palladium and copper. The alloy can contain up to about 10% copper and vanadium and up to 3% of the other alloying elements.

The elongated proximal core section 11 of the therapeutic guidewire 10 is generally about 130 to about 140 cm in length with an outer diameter of about 0.006 to 0.018 in. (0.15-0.45 mm) for coronary use. Larger diameter guidewires, e.g. up to 0.035 in. (0.89 mm) or more may be employed in peripheral arteries and other body lumens. The lengths of the smaller diameter and tapered sections can range from about 1 to about 20 cm, depending upon the stiffness or flexibility desired in the final product. The helical coil 15 may be about 3 to about 45 cm in length, preferably about 5 to about 20 cm, has an outer diameter about the same size as the outer diameter of the elongated proximal core section 11, and is made from wire about 0.001 to about 0.003 in. (0.025-0.08 mm) in diameter, typically about 0.002 inch (0.05 mm). The shaping ribbon 16 and the flattened distal section 22 of distal core section 12 have generally rectangularly-shaped transverse cross-sections which usually have dimensions of about 0.0005 to about 0.006 in. (0.013-0.152 mm), preferably about 0.001 by 0.003 in. (0.025-0.076 mm).

The high strength proximal core section 11 of therapeutic guidewire 10 generally is significantly stronger, than the pseudoelastic distal portion. Suitable high strength materials include 304-stainless steel, which is a conventional material in guidewire construction. Other high strength materials include nickel-cobalt-molybdenum-chromium alloys such as commercially available MP35N alloy.

Figure 3:
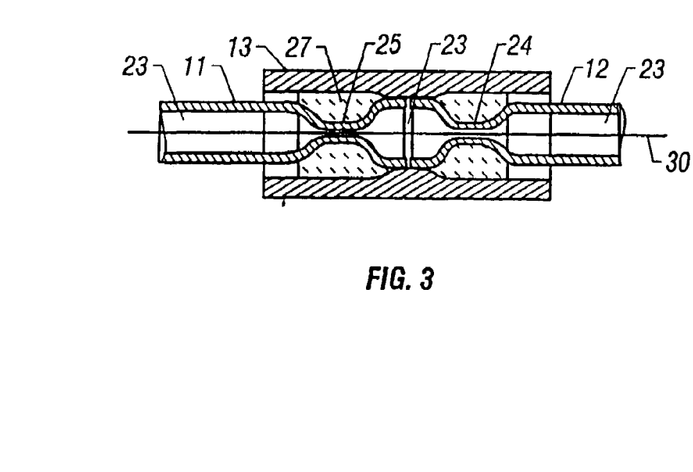
FIG. 3 is a schematic side view cross section of a connecting element embodiment of therapeutic guidewire of FIG. 1.

Turning to FIG. 3, a schematic cross-sectional side view of the connecting element 13 of therapeutic guidewire 10 of FIG. 1 is illustrated. Generally, the connecting element 13 is a hollow elongated element that receives the proximal end 24 of the distal core section 12 and the distal end 25 of the proximal core section 11. With connecting element 13, the proximal core section 11 of therapeutic guidewire 10 is in a torque transmitting relationship with the distal core section 12 of therapeutic guidewire 10. At least one optical fiber 30 is positioned within a lumen 23 longitudinally disposed through and common to the proximal core section 11, the connecting element 13 and the distal core section 12.

Continuing with reference to FIG. 3, in the therapeutic guidewire embodiment of FIG. 1, the connecting element 13 joining the hypotube-shaped proximal core section 11 with the distal core section 12 is a NiTi or SS sleeve 13 that is bonded to the distal end 25 of the proximal core section 11 (i.e., SS hypotube) and the proximal end 24 of the distal core section 12 (i.e., NiTi hypotube). Bonding of connecting element 13 may be done using a any method used in the art, for example laser bonding, thermal bonding, or using with an adhesive 27, such as Loctite, that is cured with ultraviolet (UV) light.

Figure 6:
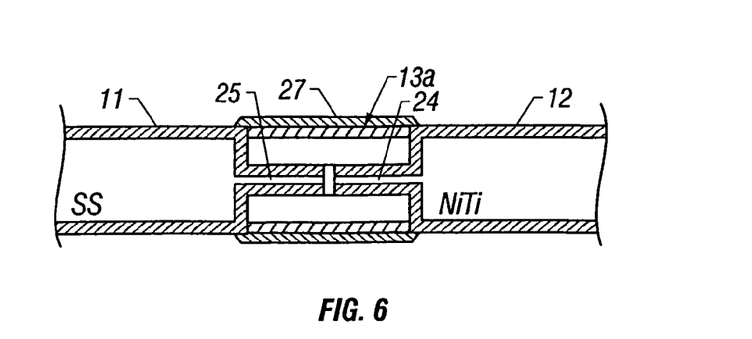
FIG. 6 is a schematic side view cross section of another embodiment of the connecting element of a therapeutic guidewire practicing this invention.
Figure 7:
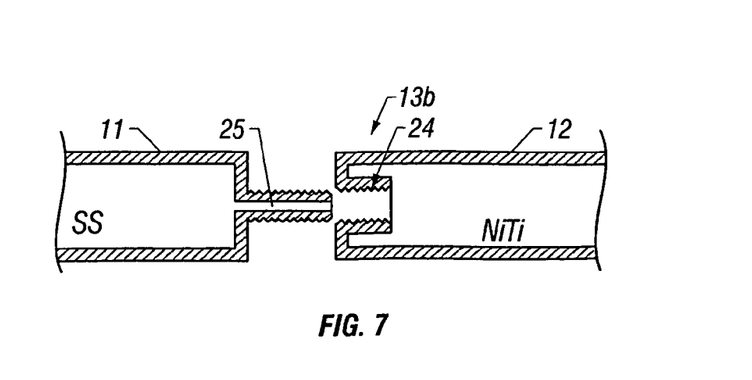
FIG. 7 is a schematic side view cross section of another embodiment of the connecting element of a therapeutic guidewire practicing this invention.

In another embodiments (shown in FIGS. 6 and 7), the connecting element 13 joining the hypotube-shaped proximal core section 11 with the distal core section 12 is a polyimide jacket (or tubing) 13a that is bonded to the distal end 25 of the proximal core section 11 (i.e., SS hypotube) and the proximal end 24 of the distal core section 12 (i.e., NiTi hypotube) with an adhesive 27, such as Loctite, that is cured using UV light (see FIG. 6). In an alternative embodiment, at the connecting element 13b, the distal end 25 of the SS hypotube 11 and the proximal end 24 of the NiTi hypotube 12 could be counterbored to form a male-female connection site (shown in FIG. 7). In this configuration, the connecting element 13 may include a NiTi or SS sleeve, a polyamide jacket (or tubing), or other configurations and materials that are advantageous to guidewire manufacture and/or guidewire use.

Connecting element 13, 13a, 13b generally have an outer diameter in the range of approximately 0.010 inch to 0.035 in., with an inner diameter in the range of approximately 0.008 inch to 0.033 in. The overall length of connector element 13, 13a, 13b may be in the range of approximately 0.25 to about 3 cm, typically about 0.75 to about 1.5 cm. In one embodiment, connecting element 13, 13a, 13b has an outer diameter of about 0.010 to 0.035 in., an inner diameter of about 0.008 inch to 0.033 in. and an overall length of 1.5 cm.

Figure 4:
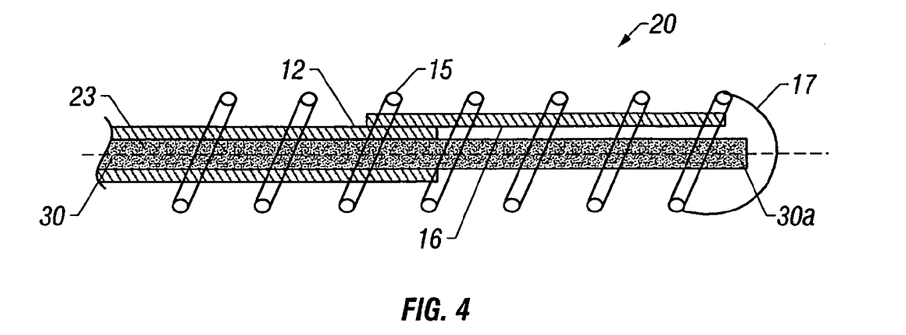
FIG. 4 is a schematic side view representation of distal core section's distal end with optical fiber of the therapeutic guidewire of FIG. 1.

Turning to FIG. 4, an embodiment of the distal most part 20 of the distal core section 12 of therapeutic guidewire of FIG. 1 is illustrated. Distal most part 20 includes the NiTi hypotube 12 (or alternatively a stainless steel, SS, hypotube) with the therapeutic guidewire flexible coil 15 attached thereto. Coil 15 may be composed of a 90% Pt-10% Ni wire with a diameter of about 0.0025 in. In this embodiment, the NiTi hypotube 12 is typically plunge-ground to a length of approximately 2 cm. Coil 15 may be trimmed to about 4 cm, inserted over the distal end of NiTi hypotube 12, and then bonded (e.g., soldered) along the edge. A shaping ribbon 16 is typically inserted under the coil 15, overlapping the distal end of the NiTi hypotube 12, and is soldered in place. At its distal end, the distal most part 20 of the distal core section 12 has a clear polymeric atraumatic guidewire tip 17 formed by coupling a clear polymeric material sheath or tube to coil 15.

Continuing with reference to FIG. 4, at least one optical fiber 30 extends longitudinally through lumen 23 of distal hypotube core section 12. As noted above, since lumen 23 longitudinally passes through the connecting element and proximal core section of guidewire, the optical fiber 30 would also extend through the connecting element 13 and proximal core section 11 (shown in FIG. 1). The optical fiber 30 may be movable within the therapeutic guidewire 10. Alternatively, the optical fiber 30 may be fixedly coupled to therapeutic guidewire 10 at various locations, for example at the connecting member 13, or at a location along the distal part 20. For optimum light transmission/reception, the optical fiber tip 30a may be disposed within the clear polymeric atraumatic tip 17.

In FIGS. 8-11, various alternate embodiments of the distal most part 20 of therapeutic guidewire 10 having at least an optical fiber 30 therein are illustrated.

Figure 8:
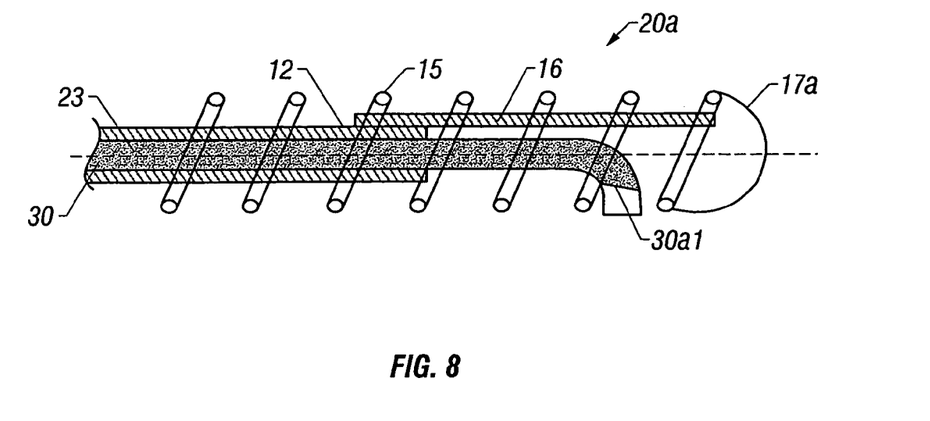
FIG. 8 is a schematic side view representation of another embodiment of distal core section's distal end with optical fiber of a therapeutic guidewire practicing this invention.

With reference to FIG. 8, in one alternate embodiment, the distal most section 20a of therapeutic guidewire 10 is configured similarly to the distal section 20 (shown in FIGS. 1 and 4) with one notable difference: instead of a clear polymeric atraumatic tip 17, a metal atraumatic therapeutic guidewire tip 17a is formed at the distal end of the therapeutic guidewire by the soldering material used to couple the distal end of coil 15 to shaping ribbon 16. With a metal atraumatic tip 17a configuration, for optimum light transmission/reception, the optical fiber tip 30a1 disposed within lumen 23 may be bent away from the centerline of distal end section 20a (as shown in FIG. 8).

Figure 9:
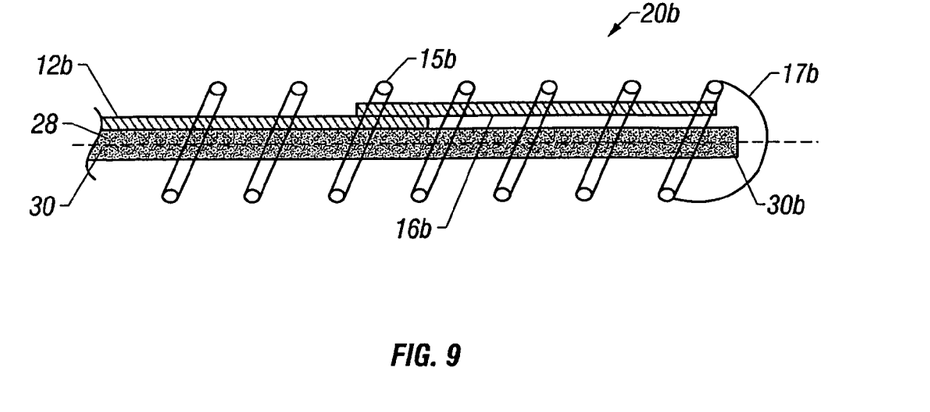
FIG. 9 is a schematic side view representation of an alternate embodiment of distal core section's distal end with optical fiber of a therapeutic guidewire practicing this invention.

With reference to FIG. 9, in another embodiment, the distal end 20b includes a therapeutic guidewire distal core 12b having a structure other than a hypotube, for example a solid tubular member. A guidewire flexible coil 15b is attached to the distal core 12b. Coil 15b may be composed of a 90% Pt-10% Ni wire with a diameter of about 0.0025 in. Coil 15b may be trimmed to about 4 cm, inserted over the guidewire distal core 12b, and then bonded (e.g., soldered) along the edge. A shaping ribbon 16b is typically inserted under the coil 15b; however, instead of overlapping the distal end of the guidewire distal core 12b, the proximal end of the shaping ribbon 16b is bonded to the distal end of the distal core 12b section, e.g. solid tubular member 12b. At its distal end, the distal most part 20b has a clear polymeric atraumatic guidewire tip 17b formed by coupling a clear polymeric material sheath or tube to coil 15b.

At least one optical fiber 30 extends longitudinally along an inside edge 28 the distal core section 12b of therapeutic guidewire 10, as well as through the channel/lumen formed in connecting element and proximal core section. The optical fiber 30 is generally fixedly coupled to therapeutic guidewire 10 at various locations, for example at the connecting member or at the distal tip 20b. Alternatively, the optical fiber 30 may be movable within therapeutic guidewire 10. For optimum light transmission/reception, the optical fiber tip 30b may be disposed within a clear polymeric atraumatic tip 17b.

Figure 10:
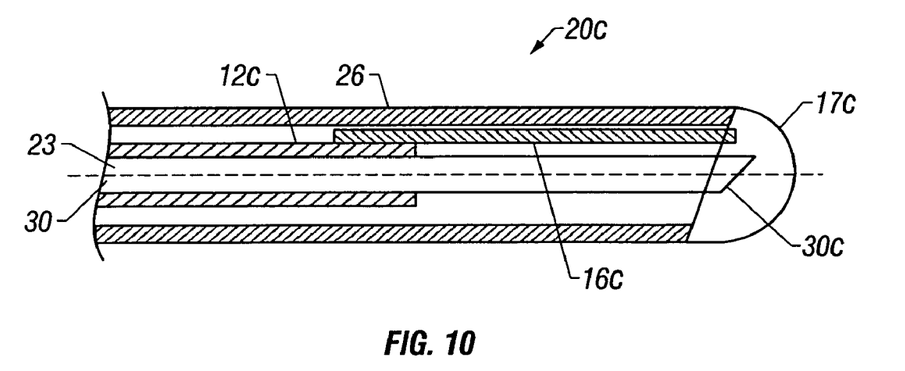
FIG. 10 is a schematic side view representation of another embodiment of distal core section's distal end with optical fiber of a therapeutic guidewire practicing this invention.
Figure 11:
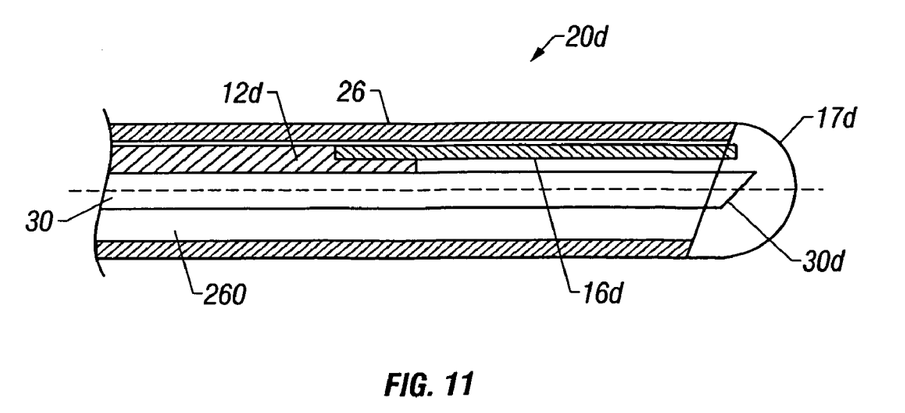
FIG. 11 is a schematic side view representation of another embodiment of distal core section's distal end with optical fiber of a therapeutic guidewire practicing this invention.

With reference to FIGS. 10 and 11, in two other embodiments, distal end 20c, 20d includes a guidewire distal core section 12c, 12d with a polymeric jacket 26 disposed over a distal end 20c, 20d portion of core section 12c, 12d. It should be noted that these guidewire embodiments do not include a flexible coil.

Distal core section 12 may be a NiTi or SS hypotube 12c (as shown in FIG. 10) or alternatively, a NiTi or SS reinforcing mandrel 12d (as shown in FIG. 11). A shaping ribbon 16c, 16d, overlapping the distal end of the guidewire distal core 12c, 12d, is soldered in place. Polymeric jacket 26 may be bonded at least at one point on outer surface of the distal core section (12c, 12d) preferably at a point closer to the connecting element 13 (shown in FIG. 1). A clear polymeric atraumatic guidewire tip 17c, 17d is formed by coupling a clear polymeric material sheath or tube to polymeric jacket 26.

At least one optical fiber 30 extends longitudinally through lumen 23 of SS or NiTi hypotube 12c of therapeutic guidewire 10 (see FIG. 10) as well as through channel/lumen formed in connecting element and proximal core section. For embodiment shown in FIG. 11, where the distal core section 12 is a reinforcing mandrel 12d, at least one optical fiber 30 extends longitudinally through lumen 260 of polymeric jacket 26, immediately below reinforcing mandrel 12d, as well as through channel/lumen formed in connecting element and proximal core section.

The optical fiber 30 may be movable within therapeutic guidewire 10. Alternatively, the optical fiber 30 may be fixedly coupled to therapeutic guidewire 10 at various locations, for example at the connecting member 13 (shown in FIG. 1), or at the distal tip 20c, 20d. For optimum light transmission/reception, the optical fiber tip 30c, 30d may be disposed within a clear polymeric atraumatic tip 17.

Generally, a 30-40 cm length of optical fiber 30 is extended beyond both the proximal and distal ends of the therapeutic guidewire 10. The distal extension of the optical fiber 30 allows for any necessary steps required to make the optical fiber tip 30 flush with, or extend slightly beyond, the most distal part 20 of the therapeutic guidewire 10. Such steps may include, but are not limited to, cleaving the distal tip of optical fiber 30 at an angle (as shown in FIGS. 10 and 11) or with a perpendicular face (as shown in FIGS. 4, 8 and 9), and removing the fiber cladding as necessary to optimize light transmission/reception.

Method for Performing Treatment and Diagnosis of Vasculature

FIG. 12 illustrates generally one embodiment of at least one optical fiber 30 within a guidewire-based treatment system 100 coupled to a data processing system 105. According to an embodiment of the present invention, the optical fiber 30 provides both a sensing/detection capability and a coupling means to the data processing system 105. Guidewire-based treatment system 100 with at least one optical fiber 30 may include any of the guidewire embodiments discussed above and shown in FIGS. 1-11.

With reference to FIG. 12, in an embodiment, the guidewire-based treatment system 100 includes a therapeutic guidewire 101 having at least one optical fiber sensor 30 longitudinally disposed therethrough. Generally, therapeutic guidewire 101 extends from a hub or connector 104 that connects therapeutic guidewire 101 to a data processing system 105. A distal portion of therapeutic guidewire 101 is insertable into a patient according to commonly known methods.

Depending upon the medical procedure being performed, the therapeutic guidewire 101 may be operatively coupled to an intravascular/intraluminal treatment device 102, such as a catheter, a stent deployment device, a drug delivery device, a radiation delivery device, and other treatment devices used in the art. If a catheter-type device is to be used, for example for performing a vessel deployment procedure or for radiation treatment, the treatment device 102 may include a balloon 103 disposed at the distal end of device 102.

Hub 104 accommodates at least one optical fiber 30 (as shown in FIG. 1). The optical fiber sensor 30 can be connected to a laser source 106 via connecting optical fiber 31. An amplifier 108, a signal processing unit 110, and a computer system 112 may be connected to process the feedback signal received through the fiber optics 30, 31. Laser source 106 can be any continuous-wave signal or a high-repetition-rate pulsed laser. In one embodiment, laser source 106 is a modulated light diode or high-powered laser light source.

The laser source is typically chosen based on the light wavelengths and light source power that facilitate the detection of the particular physical characteristic or variable. Specifically, because the light transmission window of blood is in the red to infrared (IR) range, a light wavelength in the range of 700 nm to 1500 nm may be used. It should be noted that longer wavelengths in the above stated range are desirable as they overcome some of the signal loss due to scattering in the blood. The shorter wavelengths are more energetic and therefore have the potential to cause tissue damage. In one embodiment, a wavelength of approximately 1300 nm may preferably be used.

The light output could be filtered if desired, as a homogenized illumination improves the signal-to-noise ratio. If the red or near-IR spectral range is used, laser diodes could be used as the excitation source to further improve the signal-to-noise ratio. Signal processing unit 110 typically processes a signal from visual or light source data to electronic data or vice versa.

Laser source 106, amplifier 108 and signal processing unit 110 may be connected to a computer system 112, which is typically used for data acquisition, data processing and display and system control. Guidewire-based treatment system 100 houses a optical fiber 30 which is coupled to the at least one fiber optic wire 31 to which laser source 106, amplifier 108, signal processing unit 110, and computer system 112 are connected. It is appreciated that any or all of laser source 106, amplifier 108, signal processing unit 110, and computer system 112 can be combined into an independent console unit.

It is appreciated that a variety of components can be used to help generate, transmit and receive fiber optic signals. For example, a mono-chromator can be used to receive light signals transmitted back from the field of interest. The mono-chromator can also be fitted with a photodiode array detector, such as a 512 element intensified silicon photodiode array detector. Furthermore, a high-resolution filter grating can be installed in the mono-chromator in order to sharpen the features displayed in the spectral response for easier peak recognition and spectral analysis. A pulse generator can be used to time the detector response from the output pulse of the laser light signal.

In a typical embodiment of the present invention, a physician, e.g. cardiologist, usually first decides which physical characteristic or variable of a vessel/treatment site is to be investigated (e.g., measured, identified). The physician will generally then insert a therapeutic guidewire with an optical fiber into the patient's vasculature and advances it to a specified location in the vasculature. The optical fiber is typically selected based on the optical fiber capability of detecting the particular physical characteristic or variable. Once the therapeutic guidewire with an optical fiber is in place, a data processing system is generally operated to transmit (or send) a plurality of light radiation signals via the optical fiber to the specified location in the vasculature. The reflected light radiation signals are transmitted via the optical fiber to a detector in the data processing system. The data processing system then processes these signals to provide information on a display so that a medical professional can view this information and determine how to proceed. The doctor may choose to perform a therapeutic procedure, such as balloon angioplasty or stenting, or decide that further treatment is not required. The doctor may decide that further information on that section of the vasculature is necessary and either continues with the same therapeutic guidewire-based optical fiber or use a different optical fiber to try to obtain different physical characteristics or variables data.

The therapeutic guidewire with optical fiber of the present invention provides several advantages over the relatively few current diagnostic devices used in the art. The diagnostic devices currently available measure properties such as pressure and/or flow rate, are limited in resolution, and are adversely affected by disturbed conditions typically found in the diseased area. In contrast, the therapeutic guidewire with optical fiber of the present invention can sense extremely small gradients of parameters throughout the human vascular system and, specifically, in the critical areas surrounding the treatment site to provide more comprehensive information on the disease state. Further, after the diagnosis has been carried out, the devices of the current art must then be replaced with a therapeutic device, whereas the present invention allows for a diagnostic and therapeutic tool in one device.

It should be noted that the fiber optic treatment guidewire system and method of the present invention are not limited to use in the vascular system only but may be advantageously employed in other body organs and structures, such as the esophagus, the stomach, the colon, the uterus, saphenous vein grafts, heart valves, and other body cavities, lumens, channels, and canals.

Thus, the present invention describes a unique medical device generally used to treat human atherosclerosis that has both diagnostic and therapeutic capabilities. The combined therapeutic guidewire and optical fiber configuration of the present invention allows the invention to sense vessel and blood characteristics, including but not limited to hemodynamic characteristics and/or thermal parameters of the diseased vessel or region surrounding the treatment site. The present invention may aid physicians, e.g. cardiologists, in development of lesion specific interventional strategies and preventative medicine for human vascular disease.

We claim:

1. An apparatus configured for being introduced into a patient's anatomy comprising:
   a therapeutic hollow guidewire having a high strength proximal core section, a flexible distal core section, a lumen extending within the proximal and distal core sections, and a distal end comprising a distal tip coil bonded to the distal core section and an atraumatic distal tip member bonded to a distal end of the coil; and
   at least one optical fiber slideably disposed within the lumen of the therapeutic guidewire, having a distal tip which is slidably positionable within the atraumatic distal tip member and which has an optically exposed configuration in which the optical fiber distal tip is in optical contact with the patient's anatomy outside the guidewire from within the distal tip member such that the optical fiber distal tip is configured for light transmission and/or reception so that the optical fiber is configured to sense and transmit diagnostic information from at least one of before, during, and after a therapeutic treatment.

2. The apparatus of claim 1 wherein the apparatus is coupled to a data processing system and the at least one optical fiber is configured to sense vessel and blood characteristics.

3. The apparatus of claim 2 wherein the vessel and blood characteristics are selected from the group consisting of hemodynamic characteristics, hematological parameters related to blood and blood components and thermal parameters of the vasculature.

4. The apparatus of claim 1 wherein the therapeutic guidewire is operatively coupled to a catheter.

5. The apparatus of claim 4 wherein the at least one optical fiber is marked with a radiopaque substance.

6. The apparatus of claim 1, further comprising a polymeric jacket disposed about the distal core section.

7. An apparatus as in claim 1 wherein the optical fiber provides an image of an element from light gathered from the element, the light being conveyed through the optical fiber.

8. An apparatus comprising:
   a therapeutic hollow guidewire having a high strength proximal core section and flexible distal core section, a coil attached to the distal core section and an atraumatic tip attached to the coil, the therapeutic guidewire configured to operatively receive a treatment device;
   a polymeric jacket disposed about the distal core section; and
   at least one optical fiber slideably disposed within the therapeutic hollow guidewire, having a distal tip that extends into said atraumatic tip in which the optical fiber distal tip is in optical contact with the patient's anatomy through the atraumatic tip which is configured for light transmission and/or reception to sense and transmit vessel and blood characteristics.

9. The apparatus of claim 8 wherein the treatment device is selected from the group consisting of intravascular device, intraluminal device, intraductal device and intraorgan device.

10. The apparatus of claim 8 wherein the apparatus is coupled to a data processing system and the vessel and blood characteristics are selected from the group consisting of hemodynamic characteristics, hematological parameters related to blood and blood components and thermal parameters of the vasculature.

11. The apparatus of claim 8 wherein the therapeutic guidewire includes a connecting member coupling the proximal and distal core sections; and
    an atraumatic distal tip formed at a distal end of the distal core section.

12. The apparatus of claim 11 wherein the atraumatic distal tip includes a clear polymeric material sheath coupled to the distal end of the flexible coil.

13. The apparatus of claim 11 wherein the polymeric jacket is coupled to at least one point along an outer surface of the distal core section, and the atraumatic distal tip is coupled to a distal end of the polymeric jacket.

14. An apparatus as in claim 8 wherein the at least one optical fiber provides an image of an element from light gathered from the element, the light being conveyed through the at least one optical fiber.

15. A system for sensing vessel and blood characteristics, the system comprising:
    a data processing system; and
    an apparatus coupled to the data processing system, the apparatus comprising a therapeutic hollow guidewire having a high strength proximal core section and flexible distal core section, a lumen extending within the proximal and distal core sections, and a distal end comprising a distal tip coil bonded to the distal core sections and an atraumatic distal tip member bonded to a distal end of the coil, and at least one optical fiber slidably disposed therein, the optical fiber having a distal tip which has an optically exposed configuration in which the optical fiber distal tip is positioned within said atraumatic distal tip member and in optical contact with the patient's anatomy outside the guidewire, the optical fiber capable to sense vessel and blood characteristics and transmit the sensed vessel and blood characteristics to the data processing system.

16. The system of claim 15 wherein the vessel and blood characteristics are selected from the group consisting of hemodynamic characteristics, hematological parameters related to blood and blood components and thermal parameters of the vasculature.

17. The system of claim 15, further comprising a polymeric jacket disposed about the distal core section.

18. A system as in claim 15 wherein the at least one optical fiber provides an image of an element from light gathered from the element, the light being conveyed through the at least one optical fiber.

19. The system of claim 15 wherein the optical fiber tip is bent away from a centerline of a distal end section of the guidewire.

20. The system of claim 15 wherein an end surface of the optical fiber tip is oriented at an angle relative to a transverse plane perpendicular to a longitudinal axis of the fiber.

21. A method of sensing vessel and blood characteristics, the method comprising:

operating a data processing system coupled to a therapeutic hollow guidewire having a lumen, a high strength proximal core section and flexible distal core section having a distal coil capped by an atraumatic distal tip, and at least one optical fiber having a distal tip slideably disposed in the hollow guidewire to be positioned in an optically exposed configuration in which the optical fiber distal tip is in optical contact with the patient's anatomy outside the guidewire from within the atraumatic distal tip of the guidewire such that the optical fiber distal tip is configured for light transmission and/or reception and such that light signals are transmitted to the desired location in the vasculature and reflected light signals are collected by the data processing system; and processing the reflected light signals to provide vessel and blood characteristics.

22. The method of claim 21 wherein the vessel and blood characteristics are selected from the group consisting of hemodynamic characteristics, hematological parameters related to blood and blood components and thermal parameters of the vasculature.

23. A method as in claim 21 wherein the optical fiber provides an image of an element from light gathered from the element, the light being conveyed through the optical fiber.

24. An apparatus configured for being introduced into a patient's anatomy comprising:

a) a hollow guidewire having a relatively high strength proximal core section, a relatively flexible distal core section, a lumen extending within the proximal and distal core sections, a distal tip coil on the distal core section, and a clear polymeric distal tip member bonded to a distal end of the coil; and b) at least one optical fiber slidably disposed within the lumen of the guidewire, having a distal tip which is within and surrounded by the clear distal tip member such that the distal tip of the fiber is in optical contact with the patient's anatomy outside the guidewire from within the clear distal tip member and is configured for light transmission and/or reception in the patient's anatomy.

* * * * *